United States Patent [19]

Pezaris

[11] Patent Number: 4,798,935
[45] Date of Patent: Jan. 17, 1989

[54] DRIVER CIRCUIT

[75] Inventor: Constantine D. Pezaris, Nahant, Mass.

[73] Assignee: Environmental Fragrance Technologies, Ltd., New York, N.Y.

[21] Appl. No.: 70,977

[22] Filed: Jul. 8, 1987

[51] Int. Cl.[4] .............................................. H05B 1/02
[52] U.S. Cl. .................................... 219/272; 219/497; 219/501; 236/46 F
[58] Field of Search ............... 219/490, 272, 492, 494, 219/497, 501, 507, 508, 509, 502; 307/252 UA, 117, 510, 252 B; 236/46 A, 46 C, 46 F

[56] References Cited

U.S. PATENT DOCUMENTS

| | | | |
|---|---|---|---|
| 3,310,714 | 3/1967 | Cargani | 317/148.5 |
| 3,708,726 | 1/1973 | Puvogel | 317/148.5 B |
| 3,826,955 | 7/1974 | Fest | 307/243 |
| 4,031,435 | 6/1977 | Zioni et al. | 323/34 |
| 4,144,552 | 3/1979 | Siballs | 361/166 |
| 4,330,702 | 5/1982 | Cheng | 219/492 |
| 4,333,019 | 6/1982 | Weigert | 307/252 N |
| 4,339,696 | 7/1982 | Jabor | 307/141 |
| 4,378,486 | 3/1983 | Yunik et al. | 219/492 |
| 4,395,621 | 7/1983 | Parker | 219/492 |
| 4,492,880 | 1/1985 | Weiss | 307/252 N |
| 4,493,983 | 1/1985 | Taggert | 219/502 |
| 4,547,657 | 10/1985 | Sticher, Jr. et al. | 307/510 |

Primary Examiner—M. H. Paschall

[57] ABSTRACT

A driver circuit having a predetermined on time and a predetermined off time provides a drive signal to a heating element of an aroma generating apparatus. The drive signal is applied during each positive half cycle of the input AC voltage while maintaining the gate of a silicon controlled rectifier saturated over the entire positive and negative cycles of the input AC voltage.

18 Claims, 3 Drawing Sheets

DRIVER CIRCUIT

BACKGROUND OF THE INVENTION

The present invention relates in general to a driver circuit, and more particularly, to a driver circuit adapted for applying an AC drive voltage over preselected time intervals to a load circuit, such as a resistance heating element of an aroma generating apparatus and the like.

An aroma generating apparatus is a device adapted for long term use in generating preselected aromas from replaceable aroma producing material contained within a housing by means of an underlying heating element. One such apparatus is disclosed in Glucksman, U.S. Pat. No. 4,631,387. These aromas, such as perfumes, air fresheners, insecticide scents and the like, are sensed by the olfactory organs which are stimulated by relatively small quantities of gases or vapors in the air as low as one part per one million parts of air. The perception of smell by an individual is such, that if a given smell persists, the individual ceases to be aware of the smell for the individual makes an accommodation to the odor which is then treated as the prevailing environment. Thus, one who first enters an aromatic environment becomes immediately conscious of the odor, but the sensitivity thereto diminishes and virtually disappears if the individual remains in the environment. When, however, the individual leaves the aromatic environment and is exposed to the outside atmosphere, he quickly senses this change.

Thus, the operation of the human olfactory system is such that it is highly responsive to a change in the nature or level of an aroma but is desensitized when the prevailing odor attains a steady state condition. In a room having an aroma generating apparatus in which an aromatic vapor is continuously exuded, persons in the room subjected to the vapor cease in time to become aware of the aroma, even though it is continuously being produced, thus serving no useful purpose.

Accordingly, there is a need for a drive circuit for operating an aroma generating apparatus which functions to freshen or scent the air in a room in which the unit is placed, which unit will function to periodically discharge into the room atmosphere bursts of aromatic vapor, the non-aromatic intervals therebetween having a duration sufficient to avoid desensitizing the olfactory response of those exposed to the vapors. In Glucksman, a bimetallic element is incorporated within the drive circuit to energize and de-energize the heating element for predetermined durations to provide an aroma burst mode and an aroma maintenance mode. There is also known in Weiss, U.S. Pat. No. 4,492,880 a drive circuit for an electrically operated stapling device which incorporates an LM 555 integrated circuit timer which is operated as a one shot. The time period during which the integrated circuit timer remains on is greater than one-half, but less than one complete cycle of the input AC line voltage. As to these circuits, the Glucksman bimetallic element has the inherent disadvantages attributable to the mechanical action of the bimetallic element, while the Weiss drive circuit is of limited duration requiring the generation of triggering signals during the negative portion of the input AC line voltage cycle.

SUMMARY OF THE INVENTION

It is broadly an object of the present invention to provide a driver circuit particularly adapted for operation of an aroma generating apparatus on an intermittent basis having predetermined on-time and off-time, which avoids one or more of the foregoing disadvantages resulting from the use of the above-mentioned prior drive circuits and which fills the specific requirements of such a drive circuit for use with an aroma generating apparatus.

In accordance with one embodiment of the present invention, there is provided a driver circuit responsive to an input AC voltage for applying a drive signal for a predetermined duration to a load circuit, the driver circuit comprising means for receiving an input AC voltage, means for providing a DC voltage related to the input AC voltage, timing means responsive to the DC voltage for generating a control signal for a selected time period which has a duration greater than one cycle of the input AC voltage, and control means receiving the control signal over the predetermined period for providing the drive signal to the load circuit when the AC voltage is in the positive portion of its cycle.

In accordance with another embodiment of the present invention, there is provided a driver circuit for applying an AC voltage during each positive portion of its cycle for a predetermined duration to a load circuit, the driver circuit comprising means for receiving an input AC voltage, means for providing a DC voltage related to the input AC voltage, timing means responsive to the DC voltage having an on state of first predetermined duration and an off state of second predetermined duration, the timing means when in the on state generating a control signal for the first predetermined duration which is greater than one cycle of the AC voltage, silicon controlled rectifier means receiving the control signal over the first predetermined duration for applying the AC voltage during the positive portion of its cycle to the load circuit.

In accordance with another embodiment of the present invention, there is provided a method of applying a drive signal for a predetermined duration to a load circuit, the method comprising receiving an input AC voltage, providing a DC voltage related to the input AC voltage, generatinng a control signal for a selected time period which has a duration greater than one cycle of the input AC voltage, and receiving the control signal over the time period for providing the drive signal to the load circuit when the AC voltage is in the positive portion of its cycle.

BRIEF DESCRIPTION OF THE DRAWINGS

The above description, as well as further objects, features and advantages of the present invention will be more fully understood by reference to the following detailed description of the presently preferred, but nonetheless illustrative, driver circuit when taken in conjunction with the accompanying drawings, wherein.

DETAILED DESCRIPTION

Figure 1:
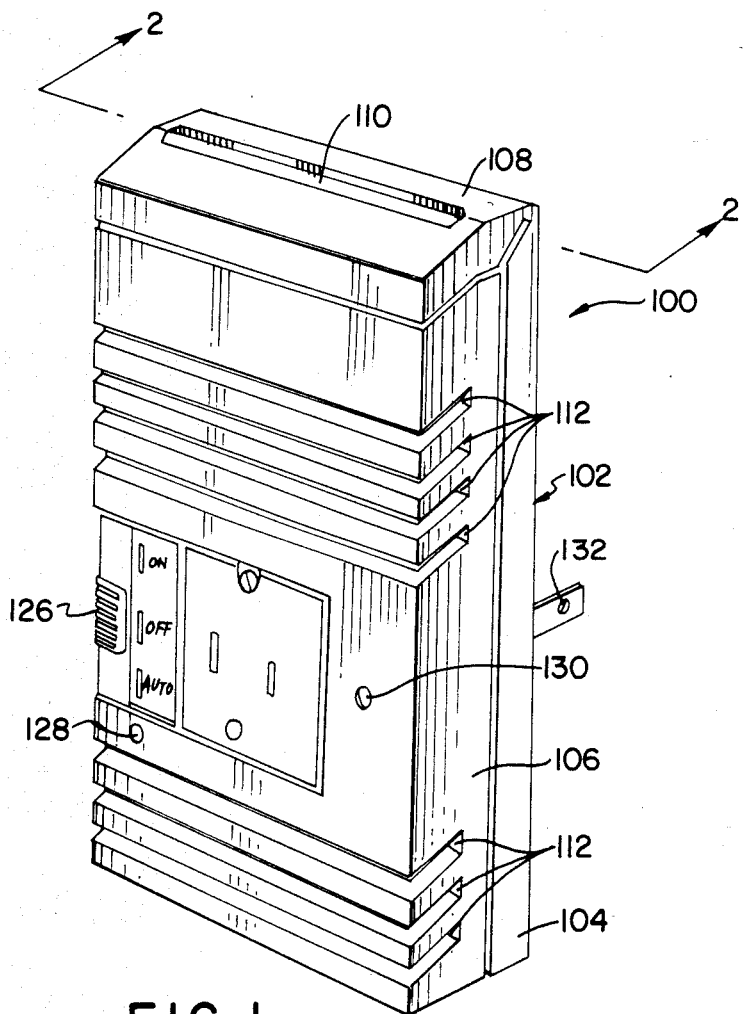
FIG. 1 is perspective view of an aroma generating apparatus adapted for discharging aromas into the surrounding atmosphere employing a drive circuit in accordance with the present invention.

Referring now to the figures, wherein like reference numerals represent like elements, there is disclosed in FIG. 1 an aroma generating apparatus 100 which includes a drive circuit constructed in accordance with the present invention. The apparatus 100 is more fully disclosed and described in co-pending U.S. application Ser. No. 065,840, filed on June 23, 1987, which is a Continuation-in-Part of U.S. Pat. No. 4,731,520. The apparatus 100 is constructed from a housing 102 generally formed of molded synthetic material such as rigid and semi-rigid plastic material. The housing 102 includes a back cover 104 and a matable front cover 106 which define a hollow region therebetween. The housing 102 is provided with an open top which is closable by means of a closure member 108 hinged to the back cover 104 and securable in a closed position. The closure member 108 is provided with a longitudinally extending opening 110 to permit liberation of aromatic vapors from the contained aroma producing material. The front cover 106 is provided with a plurality of slotted openings 112 which provide for air convection through the interior of the housing 102 and out through the opening 110 within the closure member 108.

Figure 2:
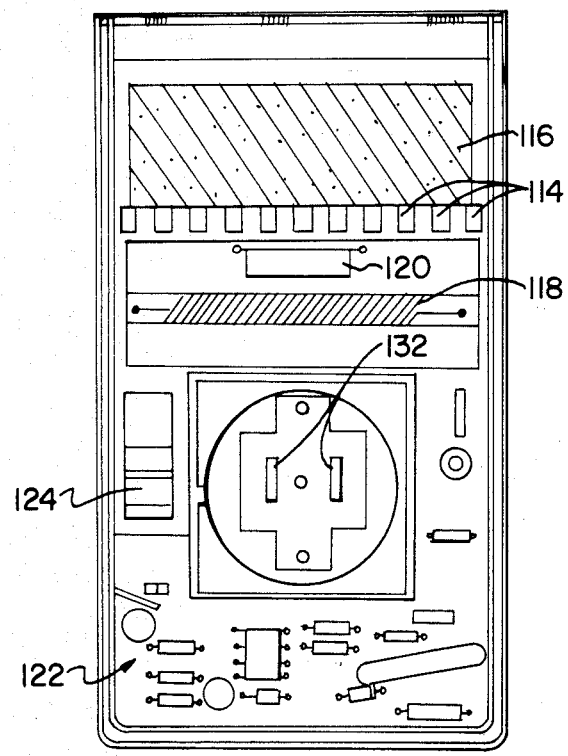
FIG. 2 is a cross-sectional view taken along the lines and arrows 2—2 in FIG. 1.

Referring now to FIG. 2, a plurality of ribs 114 extend inwardly from the back cover 104 to define a cavity thereabove. A corresponding arrangement of ribs (not shown) extend inwardly from the front cover 106. The cavity is dimensioned to receive a block of aroma producing material 116 therein through the open top of the housing 102. The aroma producing material 116 is preferably made of a porous plastic or polymer such as a porous polyethelene foam which is adapted to be impregnated with an oil based fragrance or other aroma producing chemicals.

Underlying the ribs 114, there is provided a heating element assembly which includes a wound wire resistance heating element 118 and a thermostat 120. Electric power to the heating element 118 is supplied by means of an electrical drive circuit generally designated by reference numeral 122, which is supported on a printed circuit board arranged underlying the heater element assembly 118 within the housing 102. The drive circuit 122 will be described hereinafter with respect to FIG. 3. A control switch 124 is mounted on the printed circuit board for operation of the drive circuit 122 between an off mode, on mode and automatic mode. Referring to FIG. 1, the control switch 124 is externally controlled to the desired mode by means of an external switch lever 126. An indicator light 128 is provided to indicate an on condition of the aroma generating apparatus 100 and a photocell 130 or the like is provided for automatic control of the driver circuit 122 in response to ambient light. Power from an external source such as 120 volts AC is supplied to the drive circuit 122 by means of a pair of male type electrical prongs 132 which are adapted for electrical connection with a conventional household socket.

Figure 3:
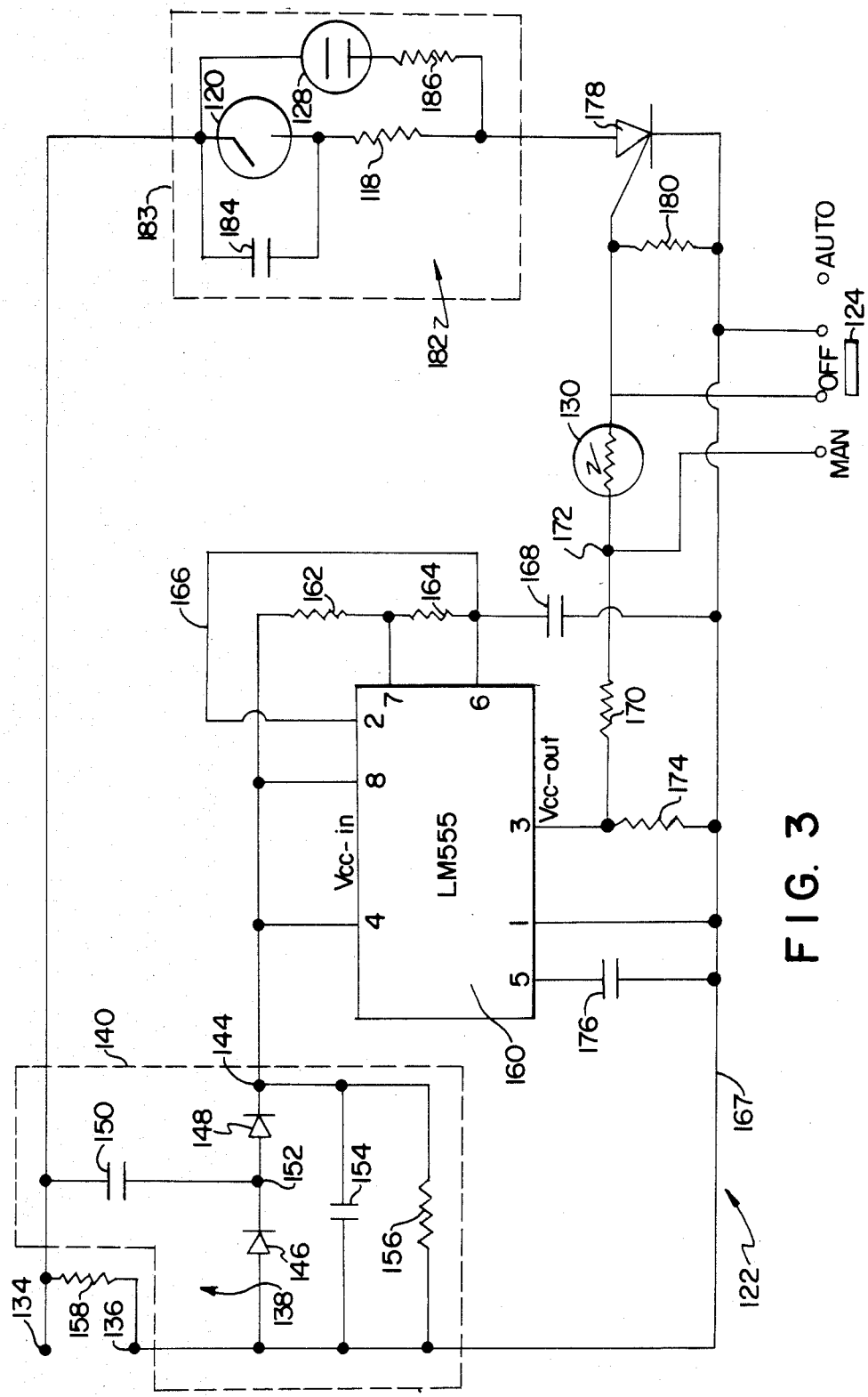
FIG. 3 is a diagram of the driver circuit in accordance with the present invention.

Referring now to FIG. 3, there is disclosed a driver circuit 122 constructed in accordance with the present invention. The driver circuit 122 includes a pair of input terminals 134, 136 for receiving an input AC line voltage, for example, 115 volts, 60 cycles. A rectifier circuit 138 contained within the dashed lines 140 is connected across the input terminals 134, 136 to provide a selected DC voltage from the input AC line voltage. The rectifier circuit 138 provides an output voltage at node 144 in the range of from 9.1 to 9.3 volts DC (Vcc in). The rectifier circuit 138 includes a pair of diodes 146, 148 arranged in series, cathode to anode, between node 144 and input terminal 136. A capacitor 150 is arranged between input terminal 134 and the junction of the cathode and anode of capacitors 146, 148 at node 152. A capacitor 154 and resistor 156 are provided in parallel arrangement with respect to each other between node 144 and input terminal 136.

A resistor 158 is provided across the input terminals 134, 136. Resistor 158 functions to discharge capacitor 150 when the line input voltage is removed across input terminals 134, 136. This condition is achieved upon unplugging the aroma generating apparatus 100 from the household outlet or other source of electrical power. The discharging of capacitor 150 by means of resistor 158 is a safety feature of the drive circuit to prevent the inadvertent application of the stored charge in capacitor 150 in the event the input terminals 134, 136 are shorted by contact with an individual.

The drive circuit 122 centers around an LM 555 integrated circuit timer 160. The DC output voltage (Vcc in) at node 144 of the rectifier circuit 138 is applied to the input of the integrated circuit timer 160 via pin 8. The reset of the integrated timer circuit 160, pin 4, is connected to the input at pin 8 to short out the reset. This shorting causes the integrated circuit timer 160 to continuously recycle, as opposed to operating as a one shot. The input pin 8 of the integrated circuit timer 160 is connected to discharge pin 7 through a resistor 162 and further to threshold pin 6 through resistor 164. Resistors 162, 164 are connected in series such that discharge pin 7 is connected to threshold pin 6 through resistor 164. In turn, threshold pin 6 is connected to trigger pin 2 via jumper line 166. A capacitor 168 is connected in series with resistor 164 to common line 167, i.e., ground.

The output of the integrated circuit timer 160 (Vcc out) is taken from pin 3 and applied through resistor 170 to node 172. Output pin 3 is further connected to the common line 167 through resistor 174. Ground pin 1 of the integrated timer circuit 160 is directly connected to the common line 167, while control voltage pin 5 is connected to the common line through a capacitor 176.

The output voltage of the integrated timer circuit 160 (Vcc out) is applied to the gate of a silicon controlled rectifier 178 through a photoswitch, photoresistor, phototransistor or photocell 130. The gate of the silicon controlled rectifier 178 is connected to common line 167 through resistor 180. Switch 124 is provided for operation of the driver circuit 122 in either the manual mode by shorting photocell 130, automatic mode or off mode by shorting Vcc out to common line 167.

The cathode of the silicon controlled rectifier 178 is connected to common line 167, while its anode is connected to a heater assembly 182 contained within the dashed lines 183. The heater assembly 182 includes the heating element 118 connected to the thermostat 120 which is shorted by a capacitor 184 to eliminate acoustic noise of the thermostat. A current limiting resistor 186 is arranged in series with the neon pilot light 128.

The operation of the driver circuit 122 will now be described. Upon application of 120 volts AC to input terminals 134, 136, capacitor 150 charges, raising node 152 to the corresponding voltage level. In the event of an open at the input terminals 134, 136, capacitor 150 will discharge through resistor 158 to prevent a potential injury to the user. Circuit 138 operates as a diode rectifier voltage reducer with filter capacitor 154. During the initial positive portion of the input cycle, diode 146 will conduct and charge capacitor 150 up to the peak value of the input waveform. As the input voltage decreases, the diode 146 will go off, but node 144 is held at output voltage Vcc in by the capacitor 154 which decays through resistor 156 with a time constant (capacitor 154×resistor 156). During the negative half cycle of the input voltage, diode 146 will discharge capacitor 150. As the input voltage increases, again diode 146 starts conducting again during which time the capacitor 154 charges back up. As the cycle repeats, the output voltage Vcc in is thus controlled to a selected value, e.g., 9.1 to 9.3 volts DC, by selecting the appropriate component values. Capacitor 150 is thus acting as a low current limiting device for rectifier 138 by supplying a limited energy charging pulse to capacitor 154 during every positive half cycle of the input AC line. The DC output voltage, i.e., Vcc in, from the rectifier circuit 138 is applied to input pin 8 of the integrated circuit timer 160.

The drive circuit 122 is an astable multi-vibrator charging and discharging capacitor 168 between one-third and two-thirds of Vcc in from the rectifier circuit 138. During the charging cycle, pin 3 of the integrated timer circuit 160 is maintained high, near Vcc out so as to provide the signal to saturate the gate of the silicon controlled rectifier 178. In the case of manual operation, control switch 124 shorts out the photocell 130. Upon saturation of the gate of the silicon controlled rectifier 178, 120 volts AC from input terminals 134, 136 is applied to the heating element 118 on each positive half cycle of the 120 volts AC, 60 or 50 Hz input. The neon pilot light 128 will light and the heating element 118 will cycle in response to the thermostat 120. Capacitor 184 across thermostat 120 filters out switching transients of thermostat 120, thus providing longer life and better control. Because the first charging cycle immediately after applying supply voltage to input terminal 134, 136 starts from 0 volts, rather than one-third Vcc in, the first on time will be approximately 30% longer than the repeat cycling time.

The on time of the driver circuit 122 is determined by the formula 0.693×(resistor 162+resistor 164)×capacitor 168. This on time corresponds to the time of charging capacitor 168 between one-third and two-thirds Vcc in. On the other hand, the off time is determined from the formula 0.693×(resistor 164×capacitor 168). The off time corresponds to the discharge time of capacitor 168. During charging of capacitor 168, the output voltage Vcc out from pin 3 of the integrated circuit timer 160 is applied to the gate of silicon controlled rectifier 178. Thus, the gate of the silicon controlled rectifier 178 is maintained saturated during both positive and negative cycles of the AC line voltage during the entire duration of the on time of the driver circuit 122. This arrangement avoids the necessity of having to trigger the gate of the silicon controlled rectifier 178 during each positive cycle of the input line voltage. To protect the gate of the silicon controlled rectifier 178 from being burnt out due to high current or voltage, resistor 170 is provided as a current limiting resistor, while resistor 180 is provided as a voltage limiting resistor.

The above calculations for determining the on time and off time of the driver circuit 122 are based on a constant output voltage Vcc in from the rectifier circuit 138 during a full cycle of operation. In the driver circuit 122, as thus far described, voltage variations of the power line can be generally neglected. However, the internal power supply has moderate regulation, so in order to obtain reasonable time accuracy, the current at node 144 of the rectifier circuit 138 should be stabilized. This is achieved by the combination of resistors 170, 174 which balance the current from the integrated circuit timer 160 in the on mode when the integrated circuit timer draws less internal current. Resistor 174, when capacitor 168 is charged and pin 3 is maintained at the output voltage Vcc out, bleeds additional current off the output voltage to keep the voltage constant. This provides compensation for differences in the charging and discharging currents required of the integrated circuit timer 160. That is, while the output voltage at pin 3 varies in step fashion during charging and discharging, being essentially zero during charge and Vcc during discharge of capacitor 168, with corresponding changes in load current through resistor 174, the voltage at pin 8 remains virtually constant, thus ensuring accurate timing.

The off time of the driver circuit 122 corresponds to the discharging time of capacitor 168. Upon capacitor 168 achieving a voltage of two-thirds the output voltage Vcc in of the rectifier circuit 138, threshold pin 6 is actuated and capacitor 168 is discharged through resistor 164 and pin 7 which is connected to ground. Resistor 162 prevents the grounding of Vcc in through pin 7 during discharge of capacitor 168. The charging of capacitor 168 through resistors 162, 174 and discharging through resistor 164 prevents the generation of a square wave form of 50% duty cycle. This precludes the ability to give equal off time and equal on time, thereby providing that the discharging time will be less than the charging time. However, by judicious selecting of values for 162, 164 and 168, the variance from an ideal equal on and off time can be made negligible.

In the automatic mode, control switch 124 is thrown to the right to place photocell 130 or other photosensitive element in line between output pin 3 of the integrated circuit timer 160 and the gate of the silicon controlled rectifier 178. The photocell 130 functions as a variable resistor in series with resistor 170. Therefore, photocell 130, resistor 170 and resistor 180 function as a voltage divider. When the photocell 130 resistance is high, the gate voltage of the silicon controlled rectifier 178 becomes too small to trigger the silicon controlled rectifier. This condition is achieved in darkness and at low light levels. On the other hand, when the photocell 130 resistance is low, the gate voltage to the silicon controlled rectifier 178 becomes sufficiently high to trigger the silicon controlled rectifier. This condition occurs under full light conditions and those conditions sufficient to provide the photocell 130 with the required resistance. Resistor 180 can be varied within limits to determine the light threshold for actuation of the photocell 130 so as to increase or decrease the sensitivity of the driver circuit 122.

Although the invention herein has been described with reference to particular embodiments, it is to be understood that these embodiments are merely illustrative of the principles and applications of the present invention. It is to be understood that numerous modifications may be made to the illustrative embodiments and that other arrangements may be devised without departing from the spirit and scope of the present invention as defined by the appended claims.

What is claimed is:

1. A driver circuit responsive to an input AC voltage for applying said input AC voltage for a predetermined duration to a load, said driver circuit comprising means for receiving an input AC voltage, means for providing a DC voltage related to said input AC voltage, timing means responsive to said DC voltage for generating a continuous control signal for a selected time period which has a duration greater than one cycle of said input AC voltage and corresponding in duration to said predetermined duration, and control means receiving said control signal over said selected time period for applying said input AC voltage to said load through said control means when said input AC voltage is in the positive portion of its cycle, said input AC voltage applied to said control means when said input AC voltage is in both the positive and negative portions of its cycle.

2. The driver circuit of claim 1, wherein said timing means comprises an integrated circuit timer.

3. The driver circuit of claim 1, wherein said timing means has an on state of first predetermined duration and an off state of second predetermined duration.

4. The driver circuit of claim 3, further including means for setting the duration of said first predetermined duration and the duration of said second predetermined duration.

5. The driver circuit of claim 1, wherein said control means comprises a silicon controlled rectifier.

6. The driver circuit of claim 1, wherein said preselected period has a duration greater than a plurality of cycles of the input AC voltage.

7. The driver circuit of claim 1, wherein said load comprises a heating element.

8. The driver circuit of claim 1, further including means responsive to light arranged between said timing means and said control means, said means permitting the application of said control signal to said control means in response to the presence of a predetermined level of light.

9. The driver circuit of claim 1, further including means for generating an aroma in response to the operation of said driver circuit.

10. A driver circuit for applying an AC voltage during each positive portion of its cycle for a predetermined duration to a load, said driver circuit comprising means for receiving an input AC voltage, means for providing a DC voltage related to said input AC voltage, timing means responsive to said DC voltage having an on state of first predetermined duration and an off state of second predetermined duration, said timing means when in said on state generating a continuous control signal for said first predetermined duration which is greater than one cycle of said AC voltage, and a silicon controlled rectifier receiving said control signal over said first predetermined duration for applying said AC voltage through said silicon controlled rectifier during the positive portion of its cycle to said load, said input AC voltage applied to said silicon controlled rectifier when said input AC voltage is in both the positive and negative portions of its cycle.

11. The driver circuit of claim 10, wherein said timing means comprises an integrated circuit timer.

12. The driver circuit of claim 10, further including means for generating an aroma in response to the operation of said driver circuit.

13. The driver circuit of claim 10, further including means for setting the duration of said first predetermined duration and the duration of said second predetermined duration.

14. The driver circuit of claim 10, wherein said first preselected duration has a duration greater than a plurality of cycles of the input AC voltage.

15. The driver circuit of claim 10, further including current control means in operative association with the timing means for maintaining said control signal at a constant DC voltage.

16. The driver circuit of claim 10, wherein said means comprises a resistor attached between an output of said timing means and a ground.

17. A method of applying a drive signal for a predetermined duration to a load, said method comprising receiving an input AC voltage, providing a DC voltage related to said input AC voltage, generating a continuous control signal for a selected time period which has a duration greater than one cycle of the input AC voltage and corresponding in duration to said predetermined duration, and applying said control signal to the gate of a silicon controlled rectifier over said selected time period for applying said input AC voltage to the load through said silicon controlled rectifier when the input AC voltage is in the positive portion of its cycle, said input AC voltage applied to said silicon controlled rectifier when the input AC voltage is in both the positive and negative portions of its cycle.

18. The method according to claim 17, further including applying said input AC voltage to a heating element of an aroma generating apparatus in response to said control signal.

* * * * *